United States Patent [19]

Scheiwe et al.

[11] 4,327,799

[45] May 4, 1982

[54] PROCESS AND APPARATUS FOR FREEZING LIVING CELLS

[75] Inventors: Max W. Scheiwe; Günther Rau, both of Aachen, Fed. Rep. of Germany

[73] Assignee: Helmholtz-Institut fur Biomedizinische Technik, Fed. Rep. of Germany

[21] Appl. No.: 125,268

[22] Filed: Feb. 27, 1980

Related U.S. Application Data

[62] Division of Ser. No. 49,302, Jun. 18, 1979, Pat. No. 4,304,293.

[51] Int. Cl.³ .............................................. F25B 13/00
[52] U.S. Cl. .......................................... 165/2; 165/12; 165/30; 62/62; 62/78; 62/157; 236/78 B
[58] Field of Search .................. 165/2, 12, 30, 61, 63, 165/64; 62/62, 64, 65, 78, 209, 418, 514 R, 157; 236/78 B, 15 BB; 128/112; 435/2; 424/101

[56] References Cited

U.S. PATENT DOCUMENTS

| | | |
|---|---|---|
| 2,964,920 | 12/1960 | Staebler ................................ 62/60 |
| 3,875,754 | 4/1975 | Faust et al. ............................ 62/60 |
| 4,004,975 | 1/1977 | Lionetti et al. ...................... 62/62 X |
| 4,018,911 | 4/1977 | Lionetti et al. ...................... 424/101 |
| 4,030,314 | 6/1977 | Strehler et al. ........................ 62/65 |
| 4,059,967 | 11/1977 | Rowe et al. ............................. 62/64 |
| 4,107,937 | 8/1978 | Chmiel .................................... 62/64 |
| 4,117,881 | 10/1978 | Williams et al. ........................ 165/2 |
| 4,199,022 | 4/1980 | Senkan et al. .......................... 165/2 |
| 4,199,954 | 4/1980 | McGill .................................... 62/62 |
| 4,251,995 | 2/1981 | Pert et al. ............................... 62/60 |

Primary Examiner—Albert W. Davis
Assistant Examiner—Margaret A. Focarino

[57] ABSTRACT

The process for freezing cell suspensions by locating the suspension in a freezing chamber and simultaneously monitoring the temperature of the suspended cells and of the chamber. The cooling of the chamber is regulated at predetermined rates in response to give temperature levels of the sample. The cooling chamber includes a fan, a heater, and a source of refrigerant. The process includes the steps of selectively decreasing and increasing the temperature of the freezing chamber responsive to predetermined temperature points on the freezing curve of the cell sample.

12 Claims, 5 Drawing Figures

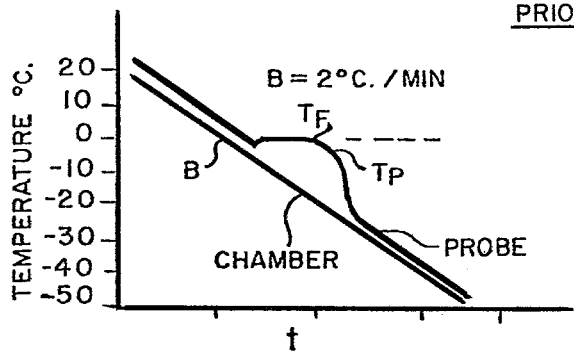
FIG. 1.
PRIOR ART
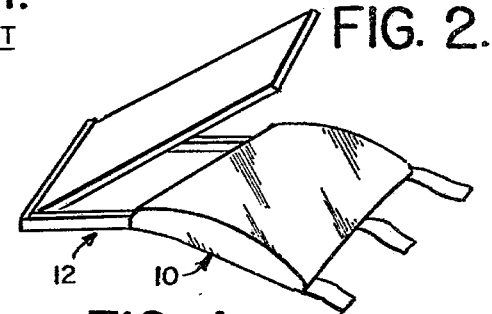
FIG. 2.
FIG. 3.
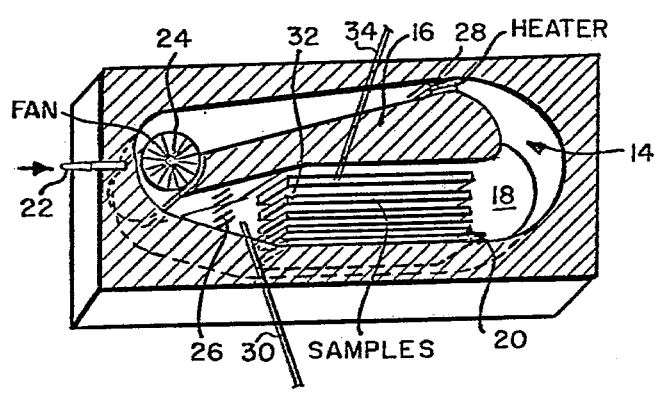
FIG. 4.
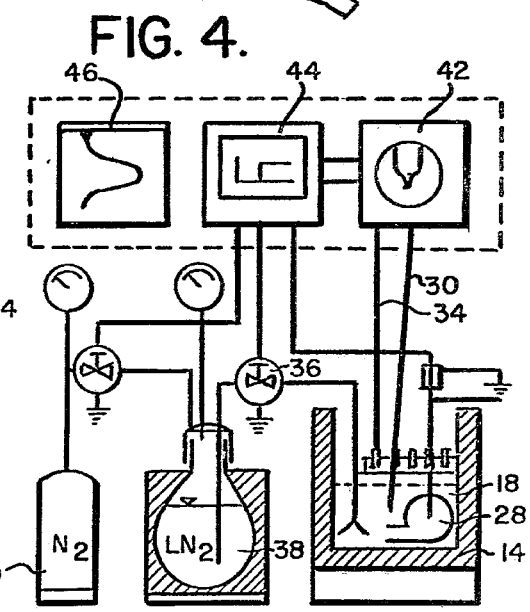
FIG. 5.
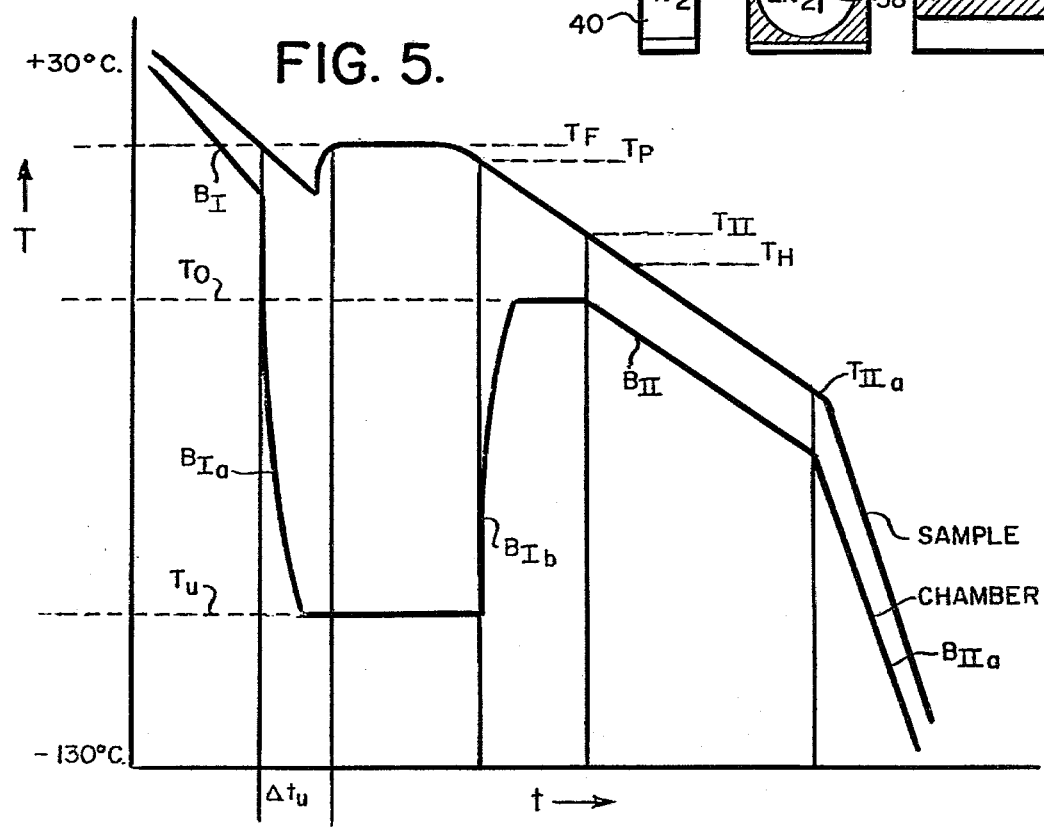

PROCESS AND APPARATUS FOR FREEZING LIVING CELLS

This is a divisional application of Ser. No. 49,302 filed June 18, 1979, now U.S. Pat. No. 4,304,293.

BACKGROUND OF THE INVENTION

The present invention relates to a process and apparatus for freezing living cells.

In recent years processes for the treatment of cancers and tumors have been developed in which, after chemotherapy, the patient is transfused with specific body cells. Since it is not possible, because of the danger of fatal rejection, to use cells of donors other than the patient himself, it has been necessary to remove the specific body cell from the patient, prior to treatment and then store such cells until they are needed. To this end it is necessary to store the withdrawn cells for prolonged periods, often several months. To preserve such cells cryogenic preservation at low temperatures, have been employed since it is yet no other means available to store living cells.

Relatively large quantities of such cells are needed for the post-therapy infusion and most importantly, such large quantities must have a relatively large ratio of living cells. Nevertheless, none of the known cryogenic freezing processes is capable of freezing large cell quantities in a single sample nor are such processes capable of maintaining the high levels of living cells required for optimum therapeutic purposes. While the importance of improved cancer therapy might justify a high cost level, it is almost impossible, no matter at what cost, with the current processes to obtain the required large quantity of cells as for example autologous lymphoid blood corpuscles or medullar cells.

There are several factors in the cryogenic preservation processes which are extremely important. Among these are the steps of:

(1) The taking of the cell sample from the blood, marrow or tissue and the concentration therefrom of the required cell type;

(2) The transfer of this concentration to a freezing container;

(3) The mixing of the concentrated sample with a freeze protectant;

(4) The controlled freezing of the specific sample;

(5) Prolonged storage below minus 130° C. (143° K.); and (6) Thawing of the sample in precise time/temperature relationship; and revitalization of the cells, i.e., their gradual dilution and elutriation.

Of the foregoing factors the most vital step and the one which has up until now presented the greatest difficulty is the controlled freezing of the sample.

According to the known freezing processes the cell samples were placed in closed freezing chambers wherein the temperature was reduced at a constant rate. It was found, however, that the cooling curve of the sample did not conform to the linear curve of the temperature drop in the cooling chamber, nor did the cooling curve of the temperature take into account the cooling curve of the sample, but to the curve as seen in FIG. 1. The sample would initially follow the curve of the temperature of the chamber, until a point below the freezing level $T_F$ at which time it would rise to a plateau defined at its upper limit by the freezing temperature $T_F$ and its lower limit $T_P$ (phase transformation temperature) constituting a pleateau where it would remain for some time. After some minutes, the temperature of the sample would again drop below the plateau $T_p$ at an extremely steep descent until it almost reaches the curve of the chamber temperature and thereafter follows in parallel the curve of the chamber temperature. Therefore, freezing processes have been developed which take into account the described abnormal thermal behaviour of aqueous samples. But, these processes don't take into account the acctual freezing curve of the freezing samples, i.e. they don't use the sample's temperature for the regulatory system. Because of practical problems, the sample's mass is mostly not equal to the mass, the freezing curve has been established for. In this case, the freezing chamber generates a freezing curve of the samples which may be similar to that shown in FIG. 1, resulting in increased damage to the cells. The slightest variations from the freezing curve of the chamber for the particular cell drastically reduces the number of living cells in the sample and produces undesirable ice crystals and other harmful effects. Furthermore, all of the freezing units currently available, freeze laboratory samples only, that is, small samples having a volume no greater than about 2 ml. Consequently, the known freezing systems do not meet the increased requirements of large quantities of cells for broad spectrum therapy.

To be therapeutically effective, large quantities, as for example in the case of medullar cells, lymphocyte cells, granulocyte cells, amounts of about $1 \times 10^{10}$ (range $1 \times 10^9$ to $1 \times 10^{11}$) are required and for thrombocytes (platelets) amounts of about $1 \times 10^{11}$ (range $1 \times 10^9$ to $1 \times 10^{11}$) are required. These increased requirements can not be met by the prior art, since (a) the cells must be frozen in volumes of about 100 to 200 ml in each unit sample, as otherwise the loss of time and sterility in filling smaller samples is too great. Sterility is insured in the prior art only, when the techniques of transfusion medicine are used and the storage of small samples is very expensive. For example, the refrigerant costs for storing a vessel of volume of 320 liters are approximately 10,400 DM (about $6,000) annually. The present invention permits the collection and storage of large amounts and at reduced costs.

(b) The therapeutic dose must contain after thawing at least 80% living cells as otherwise a lesser amount of living cells is ineffective in carrying out the vital therapeutic function. In the prior art test cells are sufficient at 50% viability, while generally, the best of the prior art samples do not produce more than 70% viable cells. On the other hand, cells frozen by the present invention have viable concentrations normally between 80–90% and sometimes to about 95% or more. Of course, not only the viable concentrations of cells give therapeutic effectiveness, but also the absolute number of living cells, which is the total recovery. This is the viable concentration times the absolute number of cells ready for transfusion divided by the number of cells originally in the sample before freezing. Though a sample may for example contain more than 70% viable cells, a total recovery may be near 10%. When cells are frozen by the present invention, the total recovery exceeds 80% on an average.

(c) Commercial freezing equipment show temperature fluctuation in the freezing chamber in about a theoretical value of ±3° C. This fluctuation in temperature reduces the viability of the cells along the edge zones of the container and reduces the viability even more.

(d) The known commercial freezing units have a temperature/time function which is not influenced by the behavior of the sample itself, but only by the behavior of the freezing chamber. Therefore, the freezing in such equipment will proceed in the desired manner only if the sample volume is not changed relative to the predetermined setting, and irrespective of the actual freezing of the sample itself. Thus, when different sample geometry is used, a new program control must be employed with such freezing units. On the other hand, the control system according to the present invention renders such a step unnecessary.

In order to avoid the foregoing difficulties, and to obtain the objects of the present invention, the present invention proposes to use not only the temperature of the freezing chamber itself but a measured temperature of the sample being frozen for the control of the various phases of the cooling process and to determine both the sample and chamber temperatures simultaneously.

SUMMARY OF THE PRESENT INVENTION

According to the present invention, a process of freezing cell suspensions within a freezing chamber is provided comprising the steps of lowering the chamber temperature at a first defined cooling rate to a given temperature value at which time the sample becomes cooled to its freezing temperature; holding the temperature of the chamber at this value until the temperature of the sample leaves the phase transformation plateau and decreases to a second predetermined temperature; heating the chamber to an intermediate temperature which is below the second predetermined temperature of the sample; maintaining the temperature of the chamber at the intermediate temperature until at such time as 85% of the mass of the sample is present in a frozen state, and; thereafter lowering the chamber temperature at a second defined cooling rate until the temperature at which substantially all the mass of the sample is frozen. Only when these relative values are matched exactly, is it possible to freeze reproducably relatively large quantities of cell suspensions and to obtain after the thaw a high survival rate.

Further, according to the present invention there is provided apparatus for carrying out the foregoing process comprising a freezing chamber having room for the mounting of a plurality of containers each having a volume of cells to be frozen, the containers being spaced from one another to provide uniform flow of the refrigerant media. The chamber has an inlet for the refrigerant, a fan for the circulation thereof, and a heater. The chamber defines an enclosed path for circulation of the cooling and heating media. The apparatus further contains a test sample supplied with a thermocouple, and a heat sensing probe located in the chamber. In this manner the temperature of the chamber and of the samples to be frozen is constantly monitored, and the inlet of the freezing media and the heating media can be continuously and simultaneously monitored.

This apparatus is provided with a programmed control system wherein the process, aforementioned, can be automatically carried out. The program control may be a micro-processor the input of which, relative a such constant as predetermined cell freezing temperature, etc., can be made, and wherein the operation is made responsive to the actual temperature of the freezing chamber and samples being frozen.

The present invention further provides novel containers and freezing trays for the storage and for freezing of relatively large samples.

Still further, the present invention provides, through the use of the process and the apparatus large concentrations of living cells, having a high degree of viability.

BRIEF DESCRIPTION OF THE DRAWINGS

FIG. 1 is a graph, wherein the abscissa t is time in minutes and the ordinate T is temperature in degrees centigrade, showing the cooling curves of the chamber and the samples following the prior art;

FIG. 2 is a perspective view of a sample bag and freezing tray;

FIG. 3 is a schematic drawing of a specific freezing chamber used in the apparatus of the present invention;

FIG. 4 is a schematic drawing of the apparatus of the present invention; and

FIG. 5 is a graph similar to that of FIG. 1 showing the cooling curves for the chamber and samples according to the present invention.

DESCRIPTION OF THE INVENTION

Before turning to a description of the present invention it is to be pointed out that a great deal of literature exists on the nature of the cells in question and in particular those characteristics concerning them during freezing and upon being frozen, namely the rates at which the cells cool at a given temperature and time conditions, the plateau temperature of the cells at the freezing state, and the point at which at least 85% of the cells in any given sample are frozen. It is for this reason that the present invention does not go into such detail except wherein it is necessary for an understanding of the present invention. In speaking of cells in the present disclosure, cells, i.e. corpuscles found in the liquid portions of the body which can be extracted from blood, glandular secretions, marrow, as well as tissue cells are to be considered.

CELL COLLECTION AND PREPARATION

In general, cells intended for use in therapeutic infusion media are initially collected by known medical techniques and are separated, as from the blood, liquid or tissue, with a known cell separator such as a haemonetas med. 30 or amino cell separator under periods of two to six hours, preferably, however, within an average time of about three to four hours, or until a sufficient amount of cells is available for freezing. Another way of cell separation may be performed by density gradient centrifugation obtained by centrifugation or gravitational force, with or without specific filtering apparatus, without the use of a cell separator as described above. In many cases, the latter procedure is used to obtain thrombocytes from normal blood units. The concentration of the cell component, upon hematocrit should be at least between 20 to 50% and preferably about 35% which may contain an anticoagulant.

The hematocrit values are of great importance for the viability and recovery of the cells after the freeze-thaw cycle. This is because the cells are dehydrated during freezing and thereby dilute the extracellular medium by the outcoming water. This fact is especially important for erythrocytes preserved by HES (hydroxyethylstarch), as was shown in respective investigations. Another important fact is the aggregation tendency of white blood cells and thrombocytes, which is extremely increased when the hematocrit exceeds the desired values indicated above. The hematocrit, the concentration of the cryoprotectant and the cooling rate are dependent on one another, and this fact is responsible for the drastically decrease in recovery obtained when the indicated values are not chosen.

Tests have shown that many living cells, for example, lymphacites, are short-lived in vitro and that damage to these cells already starts before they are subjected to freezing. The amount of the damage is time dependent. In the prior art, loss of time due to the procedures for transferring the cells, filling predetermined small volume containers, was generally considerable and often lasted more than one hour over the optimum range. As damage to the cells before freezing has a multiple effect on the damage after thawing, the saving of time in the process of handling the cells leads in itself to an increased cell vitality. As will be seen hereinafter, much of the transfer operation is avoided according to the present invention.

According to the present invention, the cells are collected, i.e. by separation, in large quantities as for example, bone marrow, lymphacites, granularcites may all be collected in the range of $1 \times 10^9$ to $1 \times 10^{11}$ cells per single sample, while the thrombocites may be collected in sample amounts of $1 \times 10^{10}$ to $1 \times 10^{12}$; stem cells may be collected in the range of $1 \times 10^6$ to $1 \times 10^8$ cells per single sample.

These corpuscles being all cells capable of suspension in a fluid, are then suspended in a volume of approximately 100 to 300 ml of isotonic water or the like, as well as plasma or similar body fluids which may contain an anticoagulant. The volume is actually determined by weighing. Due, however, to the manner in which the corpuscles are obtained, the amount of cell material in any given volume is subject to fluctuation and it is not known for cell separation what quantity of the required cell is obtained. Therefore, by extracting large volumes of blood marrow or the like by repeated cell separation, one can be assured that at least a sufficient amount of cells is obtained at one time after separation.

Once the required cell quantity is obtained and suspended in its aqueous carrier, it is further admixed with a freeze protectant and/or stabilizers. Generally, two parts of the cell suspension can be mixed with 0.5 to 1.5 parts of the freeze protectant, such as a 20 to 40 T solution of dimethylsulphoxide (DMSO) in a 60 to 80% amino acid glucose solution. For erythrocytes cells the freeze protectant may be a hydroxyethyl starch. To this there may also be added an anti-coagulant and stabilizer.

A representative suspension may then be for example 10% DMSO, 23% amino acid glucose solution, 35% cell component, 29% plasma and anti-coagulant 3% by weight, based on total weight. The plasma may be body fluid, blood or aqueous carriers. Another representative suspension may be for example 10% polyethyleneglycol, 23% aminoacid glucose solution, 35% cell component, 29% plasma and anticoagulant 3% by weight.

With the use of a freeze protectant, the osmotic load of cells is minimized. Further delay in osmotic reaction can be obtained by placing the cell suspension in a conventional tempering bath.

The collection of such large samples and the suspension thereof in protective solutions, lends itself to the direct filling of large flexible bags, such as those seen in FIG. 2 and generally depicted by the numeral 10, which can be shaped into relatively thin plates having a thickness within the range of 3 mm for approximately 100 ml volume to 10 mm for 240 ml volume. It has been found that in a thickness of between 4 to 10 mm such volumes can be easily and swiftly frozen with almost no damage to the cells. Secondly, the use of flexible bags enables the sample to be more easily handled before freezing, during the freezing process, during thawing, and during the infusion into the patient thereafter; allowing the single bag to be disposed of as a throw-away item after use. High sterility is maintained at relatively low cost. Further, such bags may be hermetically sealed by electric welding or heat welding avoiding problems of leakage inherent in the currently used sheetmetal bottles, sheetmetal plates, sheetmetal containers or other sheetmetal containers which are simply plugged with a stopper. Suitable flexible bags can be formed of polyethylene polyamide, teflon, kapton or polypropylene-components which are generally inert to the plasma body fluid and human cell.

THE APPARATUS

For the freezing process itself, the flexible bags are placed in a metal outer tray generally depicted by the numeral 10, as seen in FIG. 2. These trays comprise a bottom and a cover hinged together along one side and having interleafing side edges. These metal trays are highly heat conductive and have the advantage in allowing manipulation of the bags without damage thereto. Furthermore, the metal trays allow the flexible bag to assume an exact shape optimum for the freezing. That is, the flexible bag may be placed with as large a surface area relative to the desired thickness indicated above. Thus, the containers themselves may have a thickness of anywhere between 4 to 10 mm range. For convenience and greater accuracy in use, a series of containers in the ranges set forth above may be supplied with each freezing unit. The covered trays are preferably formed of copper sheet of approximately 2 mm thickness and may be provided with means for clamping the tray and cover together.

As seen in FIG. 3, the freezing apparatus may be made of an insulated parallelepiped housing 14, having a hollow interior in which is located a central insulated or insulating core 16 defining a continuous oval duct 18; one portion of which defines per se the freezing chamber 20, in which are located open shelves or wall flanges on which the collecting trays 12 may be mounted so as to be spaced one from each other to permit circulation around and about each tray. An inlet 22 for the introduction of the freezing media such as a source of pressurized liquid nitrogen ($LN_2$) extends through the housing wall. A fan 24 and suitable baffles 26 for equalization of the flow of the media are arranged between the inlet and the freezing chamber. A heating unit 28 such as an electric coil, provided with relay switch 29 is located downstream of the freezing chamber. Extending into the freezing chamber is a thermal transducer 30 in the form of a probe capable of sensing with great accuracy the instantaneous temperature of the freezing chamber and converting the same into an electrical signal.

At least one of the freezing trays 32 is supplied with a pair of thermocouples 34 extending through the wall thereof so as to contact center of the sample the flexible sample bag held therein. The thermocouples are copper-constant thermocouples having a tip diameter of 0.5 mm and are fixed by suitable insulating spacer means through the wall of the reference tray. The reference tray is filled with a flexible bag containing a suspension consisting precisely of the components of the cell suspensions to be frozen except for the absence therein of the cell component itself. In place of the cell component, the reference sample contains an isotonic salt solution. Thus, the reference sample may contain 10% DMSO, 23% amino acid glucose solution, 35% isotonic salt solution, 29% plasma, and 3% anti-coagulant or stabilizer. The adjustment consists of variance detector, PI-section, and pulse generator containing the variable pulse-duty factor for the electromagnetic valve. The reference input is generated digitally and then converted into an analogous signal. The microprocessor used is a model Z 80 (Zilog, USA) one, in which the user programs are inserted as hard ware. The desired parts of the cooling curve are selected by code switches in a very easy way thereby avoiding errors of the operator.

The basic control for the refrigeration system according to the present invention is shown schematically in FIG. 4. The freezing chamber 18 is supplied through its inlet 22 with a source 38 of liquid nitrogen through a hydraulic or electrically controlled valve 36. The liquid nitrogen is maintained under suitable pressure in its container 38 (schematically illustrated as a Dewar vessel) by a pressure source 40 which may itself comprise nitrogen. The thermocouples 34 from the reference sample 32, and the thermal sensor 30, sensing the temperature within the freezing chamber itself, are coupled to a measuring device 42, wherein the temperatures are determined and converted into electrical signal outputs. These electrical outputs are fed to a computer control device 44 comprising a memory storage wherein a selected program (cooling rates, freezing levels, etc.) as required for the particular sample are entered and stored. The control system includes a comparator for converting the electrical signal from the thermocouples and thermosensors with the stored program and an analyzer and adequate means for controlling the operation of the supply valve 36 for the liquid nitrogen refrigerant and the operation of the relay 29 for the heating unit 28. The control system also includes a recording device by which the actual cooling curve can be visually demonstrated. It will be obvious to those skilled in the art that they or persons skilled in the art of electric or electronic control systems will be able to fashion together the specific details to form a suitable computer, recorder, input and control means, etc., without any difficulty or problem involved. Micro-processor systems, currently available, may preferably be used.

Before the sequence or cycle of the freezing process begins the desired characteristics of program are entered in the program control by quickly setting the switches of a simple microprocessor system. This data can, if desired, be changed during the freezing process so as to enable the study of variations in the cooling curves as they may effect cell vitality. Additionally, fixed programs can be entered which for example allow the checking of the existing setting data if necessary.

Strict adherence to the cooling curves of the present process are obtainable throughout the sample and not only at its center but also near its edges by employing the platelike containers described hereinbefore and by providing the continuous oval duct and freezing chamber and flow of the air through the freezing chamber. The flow rate of the refrigerant media can be maintained at about 20 m/s. In order to reduce the lamina boundary layer and/or the turbulent boundary layer along the surface and edge of the containers, the edges of the containers may be provided with special detachable shapes and forms providing low profiles and air foils. Although the chamber temperature may fluctuate about a theoretical value on the average of plus minus 0.5° C., this extremely slight fluctuation is not measurable on the sample itself which lies inside the foil itself inside the copper tray container. The resolution of the thermocouple devices is ±0.1° C. and such fluctuation within the sample itself is not measurable.

The freezing chambers design is such that the refrigerant circulates in a cylindrical or oval path. The construction of the freezing chamber permits the parallel freezing of a plurality of samples which are all pressurized with the flow in the same manner. The homogeneous flow is obtained by additional guide-plates or baffles mounted upstream of the circulating fan. The supply line for the refrigerant positioned upstream of the fan is a further reason for the only slight nominal/actual difference in the fluctuation of the chamber temperature.

The actual temperature of the cooling media in the chamber is basically a function of the $LN_2$ feed (at predetermined pressure), flow rate (fan speed) and the concurrent selective use of the heater. By employing an electric heater, the heater may be turned on and off quickly, and its heat-up and cool-time calculated with a high degree of accuracy. Thus, the selective feed of refrigerant, and use of the heater, sometimes concurrently can be made to control the chamber and sample temperature, through the sensor probes in each and the computer responsive control valves and relays.

Within the limits of the bag volume ranges disclosed and of the container thickness disclosed, the present freezing process is not critically affected. This is so because the present invention relates chamber freezing rates with the actual temperature of the samples to be frozen by simultaneous sensing of both chamber and sample temperatures and modifying one relative to the other in response to each.

A second form of container tray may be made from aluminum. Shaped samples of a volume of 100 ml, aluminum container having a wall thickness of the aluminum of 1 mm (K value of the vessel wall = 2950 W/m² ° C. The foil bag may have a wall thickness of 0.08 mm. This container may give the cell suspension to be frozen a thickness of 3 mm.

THE FREEZING PROCESS

The process of present invention lends itself to the automatic control by the computer system previously aformentioned although it is not limited to this specific form. By pre-storing within the computer system those known factors such as the freezing temperature, the plateau temperature, the phase transformation temperature as well as 85% frozen mass temperature relating to the desired curve of freezing for the given sample, as well as the initial and secondary cooling rates for the chamber, the system can thereafter be automatically controlled, without the dependence upon time for any particular step to proceed through each of the successive steps set forth. By the use of control system the data desired can be changed during the freezing process, to enable the study of variations in the cooling curves that may effect cell vitality, and to take into account the possible unknown variations in the suspensions itself. Additionally, fixed programs can be entered to allow the checking of the existing data during the freezing process per se, rather than relying upon the success of automatic control. On the other hand, it will be clear that the use of conventional freezing units may also be made with more manual controls, to carry out the present invention.

The actual freezing of the samples follows the program set forth in FIG. 5 which constitutes the process of the present invention. Samples, generally within the temperature range 0° C. to +32° C., preferably at 0° C., inserted in the foil bag and the tray container well dried on the exterior and interior are mounted within the freezing unit as previously indicated, and initially the temperature of the freezing unit is lowered at a predetermined rate $B_I$ upon which the samples to be frozen follow suit in an almost parallel curve, until the freezing temperature $T_F$ is reached. Whereupon, the temperature of the freezing chamber is reduced sharply at an increased rate $B_{Ia}$ until a level $T_U$ is obtained. During this short interval the temperature of the sample dips below the freezing point and then sharply rises back to the freezing level which is in fact the plateau at which phase transformation takes place. The phase transformation is defined at the upper level of the freezing temperature $T_F$ and at the lower level by the temperature $T_P$ which is of course slightly lower. The temperature of the chamber is thereafter maintained constant at the temperature level $T_U$ until the amount of phase transformation in the sample causes the temperature of the sample itself to dip below the lower plateau limit $T_p$. At this time, the heating unit is activated and the level of the temperature of the chamber is caused to sharply rise at a rate $B_{Ia}$ to an intermediate level $T_0$; i.e., intermediate the lower leveled $T_U$ and the temperature of the sample at this point. The temperature of the chamber is again maintained for a period of time at the level $T_0$ so that removal of the latent heat of phase transformation is almost completed. During this period the temperature of the sample decreases to a point $T_{II}$ equivalent to the condition wherein the mass of the same is no longer a radiant source of heat and where at least 85% of the mass of the sample is presumed in the frozen state. At this point the temperature chamber is further cooled at the pre-determined rate $B_{II}$ passing level $T_H$, until $T_{IIa}$ when virtually all of the remaining mass is considered frozen. The temperature of the chamber is thereafter reduced sharply along curve $B_{IIa}$ until all of the mass is frozen and reaches its lower most limit, (143K). It is noted that the temperature level $T_0$ is less than the temperature level $T_H$, preferably by at least one degree. Upon passing the point $T_H$ the heater is discontinued. The point $T_H$ is of course easily detected by the automatic control which determines the coolant consumption required to keep the chamber temperature at the desired temperature. $T_H$ is not a fixed temperature but depends rather on the actual cooling process; therefore, it is detected automatically.

The freezing point of each of the solutions or suspensions will of course be slightly different. These freezing points are well known and can be read from standard tables or can be measured osmometrically. (For example, for a 10% DMSO solution the freezing point is −4.0° C.). The automatic control detects the freezing point of the solution itself by detecting the plateau temperature of the freezing sample. This actual temperature is then used to determine $T_P$ precisely. This allows the use of simple thermocouples, which may have a slightly different output voltage than theoretically desired, which otherwise would result in misleading temperature measurements. $T_F$ is pre-stored in the control system as well, because $BI_a$ should start even when the sample supercools. This method gives accurate cooling curves, though supercooling may appear or not and may not be reproducable. In this phase i.e., at the freezing temperature, the sample present is of course in its non-frozen state. The cooling rate $B_I$ is also determinable with respect to the given suspension so that an optimum cooling rate favorable for the vitality of the particular cells is obtained. It will be found that, at cooling rate greater or lesser than the optimum, demonstrable damage (thermal shock) occurs, presumably due to transposition within the cellular membrane building blocks and the impairment of the mechanism of the active substance transport (k+Na+-pump). The transition temperature $B_{Ia}$ is of course reduced at a rapid rate to minimize the $\Delta T_U$
and in order to obtain the desired length of the freezing plateau, which is calcuable for a constant temperature of the chamber (i.e. $T_u$).

Rate of −150° C./min or greater are permissible.

The magnitude of the lower freezing limit $T_U$ effects heat transfer during the phase change of the sample, i.e., its freezing state, during which latent heat is released. It should be maintained so that a mean migration rate of the ice front within the range of 1.00 to 2. mm/min. is obtained preferably the average of 1.5 mm per minute, corresponding to a temperature plateau lasting 1.6 minutes, has proven particularly advantageous for 4–10 mm thick plates
containing white blood cells (lymphocytes, granulocytes, stem cells) or bone marrow cells. As for freezing of erythrocytes with HES, the migration rate is highly increased by lowering $T_u$ to 15 to 25 mm/min, preferably to 21 mm/min. The influence of the migration rate has been studied by variation of that parameter without affecting the other parts of the freezing curve (that are BI, BII, BIIa). The migration velocities aforementioned are optimized values. Deviations from these values resulting in either smaller or larger velocities cause damage to the cell to be frozen.

Although the action of this effect on the cells is the subject of research, it can be said that the ice front presumably compresses the cells too much at lower values and that at higher values the cells may be mechanically damaged by the growth of sharp ice crystals.

The chamber is heated at rate $B_{I}b$ generally at approximately 50° per minute
except in the case of freezing erythrocytes with HES, where BI is given a value of 400° C./min,
by connection the heating unit while the infusion of the liquid nitrogen refrigerant is either decreased or shut off completely, until the temperature of the chamber reaches the intermediate temperature $T_0$ at which the balance between the heat and the refrigerant maintains this temperature constantly. Since due to the binary or ternary nature of the generally aqueous suspensions, the sample continues to form ice by remaining just below the freezing temperature, the phase transformation plateau is maintained at a constant temperature during this period, the lower limit thereof $T_P$ being easily calculable as $T_P = T_F − 0.5°$ C.

The simultaneous lowering of the temperature of the sample during the maintenance of the chamber temperature at $T_0$ results in the further concentration of the residual solution. The level of $T_0$ at a determined difference from that of the temperature of the sample itself should be as great as the requirement for latent heat removal necessitates and for the maintenance of the desired temperature drop in the sample. It is desirable to shorten the length of these the sample is at the freezing plateau and therefore it is beneficial to optimize heat transfer therein and achieve a corresponding heat transfer during the phase when the chamber is held at $T_0$. THis is effected by the accelerated temperature rise of the chamber after passing the phase transformation temperature $T_p$. This optimal in heat transfer results from the required cooling rate $B_{II}$ and the heat transfer coefficient between outer wall of sample and the refrigerant in the interior of the chamber. This coefficient is 110 W/m$^2$ °C., as is seen from measurements on container plates in the freezing chamber. The heat transfer coefficient depends mainly on the evporation enthalpy of the refrigerant droplets charged in the chamber. Without this evaporation effect the heat transfer is 80% less, as follows from the calculation of the heat transfer coefficient from Nusselt's heat transfer law for smooth plates at the laminar boundary layer for air. The additional latent heat is released to the point where the respective eutectic reaction is obtained (a) salt water solution $-21.2°$ C.).

The eutectic point of the respective solution gives the minimum possible temperature for the existence of any liquid. Below this temperature, the whole sample is solidified when in thermodynamic equilibrium.

Until the sample has reached an intermediate point between the freezing plateau and the eutectic reaction, i.e., the point $T_{IIa}$, this process plays an important thermal roll in obtaining the advantages of the present invention. Only at this point can the sample be regarded as a frozen body without any inherent heat source and the cooling only takes place until this point is achieved by stabilizing the chamber at $T_0$. Once the sample passes through this intermediate point $T_{II}$ the chamber can then be cooled at a rate, $B_{II}$ until the sample reaches the $T_{IIa}$ level. The heating unit is turned off when the sample reaches $T_H$. When the sample temperature is reduced to the point $T_{IIa}$ at which most of the cell suspension is frozen, the cooling can be continued at the more rapid rate $B_{IIa}$ until the conclusion of the cycle. The point $T_{IIa}$ has been detected in experiments as to be that temperature, at which $B_{IIa}$ may be used without additional damage in order to shorten the time needed for freezing. In all cases, when $T_{IIa}$ is not known, $B_{IIa}$ should have the same value as $B_{II}$.

From the freezing point $T_F$ until the reaching of the point $T_{IIa}$ wherein the cooling sample reaches about $-35°$ C. considerable changes in the state of the cell and in the original homogenous suspension liquid takes place, which are of utmost importance for the vitality of the cells. After the solidification temperature $T_F$ is reached the new phase ice forms, thereby water is removed from the residual solution and the concentration of the liquid takes place. The cell reacts with release of water, which however does not occur at any desired speed but is limited by the membrane permeability of the cells themselves. When freezing more slowly than specified, the cells remain closed to the concentrated solution too long, resulting in destruction of the cells as the shrinkage is too intense and also the proteins are denatured. When cooling faster than specified, water remains in the cell after the point $T_{II}$ has been reached. It forms intracellular ice and thereby destroys the cell from within.

Studies have shown that the effects occur even with minor deviations from the specified cooling rate appropriate for the type of cell. It was surprising to see that in the process of the present invention one can cool several cell species up to 700°/min. The migration of rate of the ice front can be brought (by the action of the length of the temperature plateau) to the optimum value of the cells other than erythrocytes with HES as a cryoprotectant, to 1.5 mm/min. For erythrocytes with HES, the migration velocity is 21 mm/min.

Even those types of cells which are normally frozen at high cooling rates can likewise be frozen in a controlled manner utilizing the present system. Thrombocytes for example are frozen at 30°/min (glycerine glucose method) erythrocytes (HES-method) are frozen at 700°/min. and action on the temperature plateau is still possible in this case due to the high maximum cooling rates.

EXAMPLES (1) Lymphocytes

A sufficient quantity of lumphocyte cells are collected, and suspended in an aqueous solution of 10% DMSO, 23% amino acid glucose solution 35% cell component, 29% plasma and 3% anti-coagulant stabilizer as previously described or in any known manner, and then filled in flexible bags at about 150 ml volume. These bags are then individually inserted in a copper tray container having an inner thickness of about 5 mm which are then placed in the freezing chamber. Simultaneously, a reference sample is prepared, identical to the suspension but without the cell component and inserted into the reference copper tray.

If the obtained volume is for example 80 ml, the same flexible bag may be used as described above. Using a container having an inner thickness of 5 mm doesn't afford any new settings for the freezing process automatic control, neither does the use of a container of smaller inner thickness, i.e. 3 mm. The use of the smaller thickness gives a better filling ratio for a single bag. This example is given in order to demonstrate the universality of the regulatory system, which therefore has a very broad field of applications; as concerning to the different volumes described, all examples may be treated in that manner.

(2) Thrombocytes

A sufficient quantity of thrombocytes are collected, and suspended in an aqueous solution of 5% Glycerine, 4% Glukose, 30% plasma, 5% ACD and 56% aminoacid solution including the thrombocytes in a concentration of 800 to $1200 \times 10^3$ cells per microliter. The suspension is filled in flexible bags at about 100 ml in volume. The bags are individually inserted in a copper tray container having an inner thickness of about 3 mm which are then placed in the freezing chamber. Simultaneously, a reference sample is prepared, identical to the suspension but without the cell component and inserted into the reference copper tray. The freeze protocol is the same as described under (1), lymphocytes, except for the cooling rate, the freezing point and the plateau end which may be taken from page 29.

(3) Granulocytes

A sufficient quantity of granulocytes cells are collected, and suspended in an aqueous solution of 5% glycerine, 4% glucose, 7% Dextran T10, 23% aminoacid glukose solution, 45% cell component, 23% plasma and 3% anticoagulant as previously described or in any known manner, and then filled in flexible bags at about 150 ml volume. These bags are then individually inserted in a copper tray container having an inner thickness of about 5 mm which are then placed in the freezing chamber. A reference sample is prepared simultaneously, identical to the suspension but without the cell component. The freeze protocol is the same as described under (1) lymphocytes.

The chamber temperature is initially lowered at rate $B_I$ equal to 6° C./min. The sample temperature follows this cooling until the freezing point $T_F$ of the solution is reached. The freezing point can be read in tables or measured (osmometrically) and is e.g. for the 10% DMSO solution, etc. of the example −4.0° C. In this phase the sample is present in the non-frozen state. Upon reaching the freezing point $T_F$, the chamber is rapidly cooled at −150°/min. to $T_U$ equal to −55° C.

The end of the phase change at constant temperature is recorded when the previously determined temperature $T_p$ equal to −4.5° C. is reached. The chamber is now heated at +50°/min. by connecting the electric heating unit until it reaches the temperature $T_0$ equal to −13° C., and thereafter maintaining this temperature constant until the sample has reached −12° C. ($T_{II}$).

Upon the passing of the sample through $T_{II}$, the chamber is cooled further at the rate $B_{II}$ equal to 2° C./min until the chamber reaches $T_{IIa}$ equal to about −35° C. At the intermediate point the $T_H$ the heating unit is turned off. This occurs automatically by determination of the required cooling power to remove the heat produced by the heater after $T_0$ has been reached. At −35° C. the cooling is continued at a decreasing rate equal to 10° C./min to −130° C. This concludes the controlled freezing process.

| Example | % of living cells ± stand. dev. | total Recovery % ± stand dev. |
|---|---|---|
| (1) | 876, ± 9,3 | 83,4 ± 7,3 |
| (2) | | |
| (3) | | |
| (4) | 88,5 ± 10,6 | 84,2 ± 8,13 |
| (5) | 98,7 ± 2,3 | 75,4 ± 11,2 |
| (6) | 119,9 ± 44,3. | 98,3 ± 32,5 |

While the present invention finds obvious advantage in utilizing the flat tray-like containers, the process may be satisfactorily used for the freezing of cylindrical samples. The cells for such purposes may as for test purposes, be suspended in tubes holding a volume of 2 ml. or more. The freezing solution is the same as that described earlier and there may be however only $1 \times 10^7$ cells per sample. A reference sample in the form of a tube similarly frozen, filled and provided with a thermal couple is also employed. Although more extended cylindrical samples can be similarly cooled by the present process a sample layer thickness in the main heat releasing direction in excess of 10 mm results in a diminished cell quality value. For this reason therefore the use of large cylindrical metal bottles holding 600 ml or more, commonly used in the preservation of red blood cells, is not suitable for the more complicated freezing of other cell components.

It will be seen from the foregoing, that the process by

| Cell Type Example | Cooling rate BI | Cooling rate BII | Freezing point $T_F$ | Plateau end $T_P$ | Start BII: $T_{II}$ | $T_U$ | $T_O$ |
|---|---|---|---|---|---|---|---|
| (2) Granulocyte[a] | −6° C./min | −2 −3° C./min | −4° C. | −4.5° C. | −12° C. | −55° C. | −13° C. |
| (3) Bone marrow[a] | −2° C./min | −1° C./min | −4° C. | −4.5° C. | −12° C. | −55° C. | −13° C. |
| (4) Thrombocyte[b] | −30° C./min | −30° C./min | −2° C. | −2.5° C. | −20° C. | −65° C. | −25° C. |
| (5) Erythrocyte | −700° C./min | −700° C./min | −2° C. | −2.5° C. | −20° C. | −130° C. | −90° C. |
| (6) Medullar[a] | −2° C./M | −1° C./M | −4° C. | −4.5° C. | −12° C. | −55° C. | −13° C. |
| (7) Thrombocyte[c] | −6° C./min | −2 −3° C./min | −1.5° C | −2.0° C. | −10° C. | −50° C. | −11° C. |
| (8) Lymphocyte[d] | −4° C./min | −4 −5° C./min | −2.5° C. | −3.0° C. | −13° C. | −55° C. | −14° C. |
| (9) Granulocyte[e] | −6° C./min | −2 −3° C. | −2.5° C. | −3.0° C. | −12° C. | −55° C. | −13° C. |

[a]DMSO process (10% in the freezing solution)
[b]Glycerine-glucose process
[c]DMSO process (4% in the freezing suspension)
[d]Polyethylene process (10% in the freezing suspension)
[e]Glycerine-glukose-dextran process (5% Glycerine, 4% Glukose, 7% Dextran T10 in the freezing suspension)

The foregoing table set forth additional examples utilizing the steps previously set forth with the given parameters.

The cell suspension frozen according to the examples were stored under cryogenic storage conditions for a lengthy period of time. Upon thawing, at conventional time/temperature parameters and gradual dilution and elutriation the cell suspension ready for transfusion contains an amount of at least 20% compatible plasma or anhalogous plasma. Vitreous fusion of anhalogous lymphocytes, stem cells and thrombocytes after freezing by the described process were carried out in 24 cases, after these cancer patients had been treated by chemotherapy. No problems due to the cryopreservation of cells arose during or after transfusion.

The concentration of viable cells was determined by known in-vitro tests, including flourescence, hyper blue exclusion, specific culture tests, detection of the released cell content and counting or hematocrit determinations to be as follows.

monitoring the temperature of both the ambient chambers, and the temperature of the samples permits the use of a flexible control system, by which the advantages of the present process are obtained, without dependence upon predetermined time limit. The measured sample temperature is used for controlling the various phases of the chamber cooling. Another important aspect is the use of compensatory heating, with which the heat-up characteristic of the chamber is adjusted as needed. This results in the following advantages:

Selection of the duration of the plateau temperature to the optimum value given by sample geometry and refrigerant temperature;

Rapid determination of the cooling curve optimal with respect to recovery for a cell type/protectant combination;

Variation of the cooling rate above and below the freezing point separately and independently of the duration of the plateau temperature;

Possible changes of single sample mass as well as number of samples without change of program;

Collection of large samples and the elimination of division or filling up of the cell containers;

Optimum definition of the obtained cells from the freezing process;

Increased assurance that the samples are sterile.

Various modifications, changes and embodiments have been shown and referred to in the foregoing disclosure. Others will be obvious to those skilled in this art. Accordingly, it is intended that the foregoing disclosure be taken as illustrated only and not as limiting the scope of the present invention.

What is claimed is:

1. The process for freezing cell suspensions in a freezing chamber using gaseous or vaporizing cold nitrogen for heat transfer comprising the steps of
   locating samples of the cell suspension in a container of fixed shape,
   placing at least one of said containers in the freezing chamber,
   simultaneously monitoring the temperature of the cells in at least one container for detection of the supercooling, the freezing temperature and the length of the freeze plateau, and the temperature of the chamber,
   regulating the cooling of the chamber at predetermined rates automatically in response to the supercooling, the freezing temperature, the length of the freeze plateau, mass and geometry and heat transfer properties inside and outside the sample containers, including quick rewarming of the chamber after the end of the plateau phase during freezing,
   generating a homogeneous temperature field inside the sample containers so that each single volume element of the sample is cooled linearly and for a defined length of time, and
   providing a substantially small temperature deviation from the mean temperature at any point inside the sample containers during freezing by respectively controlling the cooling and warming of said chamber.

2. The process according to claim 1 wherein said containers are metal and have a thickness of between 4 to 10 mm, the walls of said containers having a thickness of between 1 to 2 mm.

3. The process according to claim 2, wherein said sample suspensions are first placed in a foil bag which is then placed within said metal container.

4. The process according to claim 1, 2 or 3, including the steps of lowering the chamber temperature at a first defined cooling rate $B_I$ to a given temperature value $T_U$ during which the sample becomes cooled to its freezing temperature $T_F$; holding the temperature of the chamber at this value to permit phase transformation of said sample and until the temperature of the sample decreases below the phase transformation plateau $T_P$; heating the chamber to an intermediate temperature $T_O$ which is below the temperature of the sample; maintaining the temperature of the chamber at the intermediate temperature $T_O$ until such time $T_{II}$ as 85% of the mass of the sample is present in a frozen state, and; thereafter lowering the chamber temperature at a second defined cooling rate $B_{II}$ until the temperature at which substantially all the mass of the sample is frozen, and further decreasing the temperature to a level for storage.

5. The process according to claim 4, wherein the cells are lymphocytes and the steps include cooling at the rate $B_I$ of 6° C./min to a freezing temperature $T_F$ of $-4°$ C. and a chamber temperature $T_U$ of $-55°$ C., holding the chamber temperature at this value until the sample has reached a plateau end temperature $T_P$ of $-4.5°$ C., heating the chamber to an intermediate temperature $T_O$ of $-13°$ C. and cooling the chamber at cooling rate $B_{II}$ of 2° to 3° C./min.

6. The process according to claim 4, wherein the cells are granulocytes, and the steps include cooling at the rate $B_I$ of 6° C./min to a freezing temperature $T_F$ of $-4°$ C. and a chamber temperature $T_U$ of $-55°$ C., holding the chamber temperature at this value until the sample has reached a plateau end temperature $T_P$ of $-4.5°$ C., heating the chamber to an intermediate temperature $T_O$ of $-13°$ C. and cooling the chamber temperature at a cooling rate $B_{II}$ of 2° to 3° C./min.

7. The process according to claim 4, wherein the cells are bone marrow cells, and the steps include cooling at a cooling rate $B_I$ of 2° C./min to a freezing temperature $T_F$ of $-4°$ C. and a chamber temperature $T_U$ of $-55°$ C., holding the chamber temperature at this value until the sample has reached a plateau end temperature $T_P$ of $-4.5°$ C., heating the chamber to the intermediate temperature $T_O$ of $-13°$ C. and the lowering the chamber temperature at the cooling rate $B_{II}$ of 1° C./min.

8. The process according to claim 4, wherein the cells are thrombocytes, and the steps include cooling at a cooling rate $B_I$ of 30° C./min to a freezing temperature $T_F$ of $-2°$ C. and a chamber temperature $T_U$ of $-65°$ C., holding the chamber temperature at this value until the sample has reached a plateau end temperature $T_P$ of $-2.5°$ C., heating the chamber to an intermediate temperature $T_O$ of $-25°$ C. and cooling the chamber temperature at a cooling rate $B_{II}$ of $-30°$ C./min.

9. The process according to claim 4, wherein the cells are erythrocytes, and the steps include cooling at a cooling rate $B_I$ of 700° C./min to a freezing temperature $T_F$ of $-2°$ C. and a chamber temperature $T_U$ of $-130°$ C., holding the chamber temperature at this value until the sample has reached a plateau end temperature $T_P$ of $-2.5°$ C. and heating the chamber to an intermediate temperature $T_O$ of $-90°$ C., and lastly cooling the chamber temperature at a cooling rate of 700° C.

10. The process according to claim 1, wherein the cells to be frozen are selected from the group consisting of erythrocytes, lymphocytes, stem cells, graulocytes and thrombocytes, said cells being suspended in an aqueous solution, the volume of the erythrocyte solution being between 500 to 800 ml, the lymphocyte, stem cell and granulocyte solutions being between 100 to 200 ml, and the volume of thrombocyte solution being between 25 to 100 ml.

11. The process according to claim 10, wherein the suspension includes a freeze protectant selected from the group consisting of 20 to 40% dimethyl sulfoxide solution in 60 to 80% amino acid-glucose solution, or 15 to 25% hydroxyethyl starch solution, or 4 to 6% glycerol, 3 to 5% gluctose, 6 to 10% dextran T10, or 15 to 25% polyethyleneglycol or 75 to 85% amino acid-glucose solution.

12. The process according to claims 1 or 4, wherein the migration rate of the ice front is maintained at 1.0 to 2.0 min/min. or at 15-25 min/min.

* * * * *